United States Patent [19]
LeGrow et al.

[11] Patent Number: 5,759,529
[45] Date of Patent: Jun. 2, 1998

[54] SILICONE COMPOSITION FOR SKIN CARE

[75] Inventors: Gary Edward LeGrow; John Cyrus Smith, Jr., both of Midland, Mich.

[73] Assignee: Dow Corning Corporation, Midland, Mich.

[21] Appl. No.: 145,553

[22] Filed: Nov. 4, 1993

Related U.S. Application Data

[63] Continuation of Ser. No. 13,877, Feb. 5, 1993.

[51] Int. Cl.$^6$ .................................. A61K 7/11; A61K 7/06
[52] U.S. Cl. ................................. 424/70.12; 424/78.03; 424/DIG. 2
[58] Field of Search ............................ 424/78.03, 70, 424/71, 70.12, DIG. 2

[56] References Cited

U.S. PATENT DOCUMENTS

| | | | |
|---|---|---|---|
| 4,364,837 | 12/1982 | Pader | 252/173 |
| 4,902,499 | 2/1990 | Bolich | 424/70 |
| 4,906,459 | 3/1990 | Cobb | 424/70 |
| 5,002,762 | 3/1991 | Bolich | 424/70 |
| 5,118,507 | 6/1992 | Clement | 424/401 |

*Primary Examiner*—Sally Gardner-Lane
*Attorney, Agent, or Firm*—James L. Decesare

[57] ABSTRACT

A composition for conditioning the skin which includes a silicone gum, a volatile methylsilicone fluid, and a volatile alkylmethylsiloxane. When applied to the human skin, the composition adsorbs approximately twenty percent faster, has a less greasy feel during application, and provides a coating on the skin which is smoother, than comparative products.

20 Claims, No Drawings

# SILICONE COMPOSITION FOR SKIN CARE

This is a continuation of copending application Ser. No. 08/013.877 filed on Feb. 5, 1993 pending.

BACKGROUND OF THE INVENTION

This invention is directed to a composition for conditioning the skin which includes a silicone gum, a volatile methylsilicone fluid, and a volatile alkylmethylsiloxane.

Ageing of the human skin results from a loss of elasticity. Less elasticity means that the epidermis has a reduced ability to absorb water. In order to maintain the natural functioning of the skin, it is necessary to ensure that transepidermal water loss does not exceed certain levels resulting in dry skin.

Normally adjusted skin surfaces are characterized by smoothness and suppleness. These characteristics are highly dependent upon the water content of the stratum corneum. If moisture falls below a level of about fifteen percent, skin flexibility suffers, resulting in dry, raw, and chapped skin surfaces. Fats can restore smoothness but not elasticity and flexibility. Drying out of the skin surface is a disturbance of the physiological balance between the production and use of water and fats in the epidermis and stratum corneum.

In cases where the skin has become dry, it is common to recover the natural balance with the help of external skin care preparations. These skin conditioning preparations typically are applied topically to the skin in the form of a film, in an effort to cause skin softening and relieve dryness. The film retards water loss and allows the skin to rehydrate. Thus, dry skin is prevented by protection and moisture retention.

In addition to providing the benefits noted above, the compositions of the present invention offer the additional advantages in that (i) when they are applied to the human skin, they adsorb about twenty percent faster than comparative products; (ii) they possess a less greasy feel than comparative products during their application to the skin; and (iii) they provide a coating on the skin which is smoother than comparative products.

Sensory testing revealed that comparative products were more sticky, required more rubbing in their application to the skin, and lacked the smoothness following rub in, than was possessed by the compositions of the present invention.

SUMMARY OF THE INVENTION

It is an object of the present invention to provide a skin conditioning composition which will soften the skin and relieve dryness.

It is also an object of the present invention to provide a skin conditioning composition which, when applied to the human skin, adsorbs approximately twenty percent faster, has a less greasy feel during application, and provides a coating on the skin which is smoother, than comparative products.

These and other objects, features, and advantages of the herein defined present invention will become more apparent from a consideration of the following detailed description thereof.

DETAILED DESCRIPTION OF THE INVENTION

The composition of the present invention contains three silicone components as ingredients. Two of the silicone components are volatile fluids, while the third component is a high molecular weight silicone gum.

One of the volatile fluids is a low viscosity methylsilicone fluid. The methylsilicone fluid corresponds to the average unit formula $(CH_3)_aSiO_{(4-a/2)}$ wherein a is an integer having an average value of from two to three. The methylsilicone fluid contains siloxane units joined by Si—O—Si bonds. Representative units are $(CH_3)_3SiO_{1/2}$, $(CH_3)_2SiO_{2/2}$, $(CH_3)SiO_{3/2}$, and $SiO_{4/2}$. These units are present in such molar amounts such that there is an average of from about two to three methyl groups per silicon atom in the methylsilicone fluid, and the fluid has a viscosity of less than about one hundred centistokes measured at twenty-five degrees Centigrade.

The methylsilicone fluid contains dimethylsiloxane units and optionally trimethylsiloxane units. Preferably, the methylsilicone fluid has a viscosity of less than about ten centistokes such as cyclopolysiloxanes of the general formula $[(CH_3)_2SiO]_x$, and linear siloxanes of the general formula $(CH_3)_3SiO[(CH_3)_2SiO]_ySi(CH_3)_3$, in which x is an integer having a value of from three to ten, and y is an integer having a value of from zero to about four.

Such volatile methylsilicone fluids have boiling points generally less than about two hundred-fifty degrees Centigrade, and viscosities preferably generally less than about ten centistokes measured at twenty-five degrees Centigrade, most preferably 0.65 to 5.0 centistokes.

The cyclopolysiloxanes have been assigned the adopted name "CYCLOMETHICONE" by The Cosmetics, Toiletries and Fragrance Association, Inc., Washington, D.C. (CTFA). Both the cyclopolysiloxanes and the linear siloxanes are clear fluids, and are essentially odorless, nontoxic, nongreasy and nonstinging. Cosmetically, these methylsilicone fluids are nonirritating to skin, and exhibit enhanced spreadability and ease of rub-out when applied. Once applied, the materials evaporate leaving behind no residue.

Methylsilicone fluids which are operable in accordance with the present invention leave substantially no residue after thirty minutes at room temperature when one gram of fluid is placed at the center of a No. 1 circular filter paper having a diameter of 185 mm supported at its perimeter in open room atmosphere. By methylsilicone fluid is meant a composition containing two or more silicon atoms, all of which are bonded by way of at least one oxygen atom to at least one other silicon atom and at least one methyl radical, each silicon valence not satisfied by oxygen being satisfied by a methyl radical.

Representative methylsilicone fluids found to be especially useful in the present invention are hexamethyldisiloxane which has a boiling point of 99.5 degrees Centigrade and the formula $Me_3SiOSiMe_3$; octamethyltrisiloxane which has a boiling point of 152 degrees Centigrade and the formula $Me_3SiOMe_2SiOSiMe_3$; hexamethylcyclotrisiloxane which has a boiling point of 133 degrees Centigrade and the formula $[(Me_2)SiO]_3$; octamethylcyclotetrasiloxane which has a boiling point of 171 degrees Centigrade and the formula $[(Me_2)SiO]_4$; and decamethylcyclopentasiloxane which has a boiling point of 205 degrees Centigrade and the formula $[(Me_2)SiO]_5$. These methylsilicone fluids may be used alone, or as mixtures with one another in combinations of two or more. Mixtures of more than one of the methylsilicone fluids will result in a volatile material having an evaporating behavior different from any one of the individual methylsilicone fluids. The methylsilicone fluids and their methods of preparation are known in the art, and such fluids are commercially available.

In some instances, it may be desirable to replace one or more of the methyl groups in the methylsilicone fluid with other groups. Thus, there may be substituted groups such as alkyl radicals having two to twelve carbon atoms; aryl radicals having six to ten carbon atoms; amine groups; vinyl; hydroxy; haloalkyl groups; aralkyl groups; and acrylate groups; for example.

Preferably, the volatile methylsilicone fluid is a cyclopolysiloxane, and most preferably a mixture of octamethylcyclotetrasiloxane [(Me$_2$)SiO]$_4$, and decamethylcyclopentasiloxane [(Me$_2$)SiO]$_5$.

The other volatile silicone fluid used as a component in the compostions according to the present invention is an alkylmethylsiloxane having a formula selected from the group consisting of

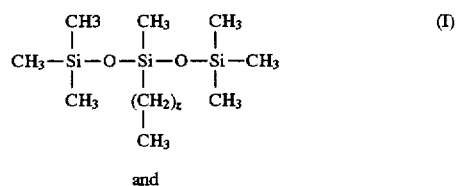

and

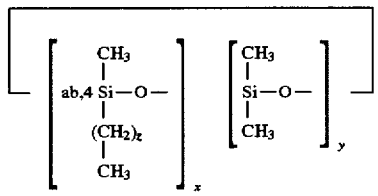

In Formulas (I) and (II) for the alkylmethylsiloxanes, the sum of the integers x and y is four, five, or six, with the proviso that x and y cannot be zero; and z is an integer having a value of one to twelve. Preferred compounds include alkylmethylsiloxanes in which (i) x is one; y is three, four, or five; and z is 5–7; in which (ii) x is two; y is two, three, or four; and z is 5–7; in which (iii) x is three; y is one, two, or three; and z is 5–7; in which (iv) x is four; y is one, or two; and z is 5–7; and in which (v) x is five; y is one; and z is 5–7. Most preferably, the alkylmethylsiloxane is the compound 3-hexyl heptamethyltrisiloxane. This compound has Formula (I) set forth above in which z is five. It is particularly preferred that the alkylmethylsiloxane have a vapor pressure greater than 0.005 mm at a temperature of 20–25 degrees Centigrade. A compound of Formula I in which z has a value of five has a vapor pressure of 0.10 mm, while a compound of Formula I in which z has a value of eleven has a vapor pressure of 0.01 mm, for example.

The third silicone component of the composition of the present invention is a high molecular weight silicone gum selected from the group consisting of (i) silanol endblocked polydimethylsiloxane gums having the formula HO(CH$_3$)$_2$SiO[(CH$_3$)$_2$SiO]$_n$Si(CH$_3$)$_2$OH, and (ii) polydimethylsiloxane gums having the formula (CH$_3$)$_3$SiO[(CH$_3$)$_2$SiO]$_n$Si(CH$_3$)$_3$. In both formulas for the silicone gums, n is an integer having a value of from five thousand to fifty thousand. Most preferably, the value of n is ten thousand to fifty thousand.

The composition containing the three silicone components includes from 30.0 to 97.8 percent by weight of the alkylmethylsiloxane, from 0.2 to fifty percent by weight of the cyclopolysiloxane, and from two to twenty percent by weight of the silicone gum. Most preferably, the composition includes from 83.5 to 94.5 percent by weight of the alkylmethylsiloxane, from 0.5 to 1.5 percent by weight of the cyclopolysiloxane, and from five to fifteen percent by weight of the silicone gum.

In use of the composition for the conditioning of human skin, the composition is applied in an effective amount necessary to form a coating on the skin, and the coating is rubbed into the skin. If desired, the composition may be applied to the skin in the form of a lotion. The lotion should include from one to ten percent by weight of the silicone composition. The lotion may additionally contain other adjuvants which are beneficial to the skin such as emollients, sunscreens, preservatives, perfumes, and fragrances. In addition to lotions, the composition can be incorporated into skin creams, facial cosmetics, and suntan oils or lotions.

Sunscreens are evaluated according to their ability to slow the erythema or sunburn resulting from the exposure of skin to ultraviolet light between 290–320 nanometers (the UV-B region). This is accomplished by absorbing damaging radiation before the radiation contacts the skin surface. Para-aminonbenzoic acid derivitives and cinnamates such as octyl methoxycinnamate are examples of preferable and commercially employed categories of sunscreen active compounds. UV-A region agents capable of absorbing ultraviolet light in the range of 320–400 nanometers are also useful in accordance with the present invention including benzophenes and materials such as butylmethoxy dibenzoylmethane. Some additional examples of sunscreen chemicals which may be employed in accordance with the present invention are 2-ethoxyethyl p-methoxycinnamate; menthyl anthranilate; homomenthyl salicylate; glyceryl p-aminobenzoate; isobutyl p-aminobenzoate; isoamyl p-dimethylaminobenzoate; 2-hydroxy-4-methoxybenzophenone-5-sulfonic acid; 2,2'-dihydroxy-4-methoxybenzophenone; 2-hydroxy-4-methoxybenzophenone; 4-mono and 4-bis(3-hydroxypropyl)amino isomers of ethyl benzoate; and 2-ethylhexyl p-dimethylaminobenzoate.

If it is desired to include a minor amount of additional materials for the purpose of facilitating the emolliency characteristics of the compositions of the invention, some appropriate materials are straight, branched or cyclic hydroxy compounds such as alcohols containing 1–30 carbon atoms; straight, branched or cyclic carboxylic acids containing 1–30 carbon atoms; acid esters containing C1 to C30 caboxylic acids esterified with C1 to C30 alcohols; alcohol ethers containing 1–30 carbon atoms; and alkanes of the formula H—(CH$_2$)$_n$—H where n is 5–30. Specific examples of some of these materials are 2-ethylhexyl oxystearate; arachidyl propionate; 2-ethylhexyl adipate; isopropyl myristate; stearyl alcohol; propionic acid; stearic acid; mineral oil; aliphatic hydrocarbons such as mineral spirits; and lanolin and lanolin derivatives such as acetylated lanolin and isopropyl lanolate. Humectants such as glycerin may also be employed.

The alkylmethyl polysiloxanes of this invention can be produced by the reaction of a linear siloxane having Si—H functionality in the chain such as (Me$_3$SiO$_{1/2}$)$_2$(OSiMeH)$_x$ in which Me is methyl and x is forty to about one hundred, and a cyclic siloxane having (Me$_2$SiO) units of the formula (Me$_2$SiO)$_x$ in which Me is methyl and x is an integer of about three to six preferably four or five. The reaction product is then contacted with a slight stoichiometric excess of an alkene CH$_2$=CHR in the presence of a platinum on carbon catalyst and an alkylmethylsiloxane having the structure shown above is produced.

The alkylmethyl polysiloxanes of this invention can also be produced by the direct hydrolysis of methylhydrogen dichlorosilane to form cyclomethylhydrogen polysiloxanes, or by the direct cohydrolysis of methylhydrogen dichlorosilane and dimethyl dichlorosilane to form cyclomethylhydrogensiloxy dimethylsiloxy copolymers. The reaction product is then contacted with a slight stoichiometric excess of an alkene $CH_2=CHR$ in the presence of a platinum on carbon catalyst and an alkylmethylsiloxane having the structure shown above is produced.

Batch production of the alkylmethyl polysiloxanes is conducted by adding the reaction product to a non-agitated suspension of the catalyst in the alkene at about sixty degrees Centigrade. Continuous production of the alkylmethyl polysiloxanes is conducted by pumping a preheated solution of a five percent stoichiometric excess of an alkene $CH_2=CHR$ and the reaction product through a packed column containing platinum on carbon catalyst chips. The column will require provision for the removal of heat because of the exothermic nature of the reaction.

The materials are further processed in accordance with the present invention in order to provide a more cosmetically acceptable product by removing from the product any remaining cyclic siloxane and any residual methylhydrogendimethylsiloxane cocyclics present as $(MeHSiO)(Me_2SiO)_3$. The alkylmethyl polysiloxanes produced in accordance with the present invention have been found to contain at most about 0.5 percent residual alkene and about 99.5 percent alkylmethyl polysiloxane product. No measurable residual amount of platinum has been detected. The products are otherwise colorless, odorless, clear and stable materials. The products are particularly adapted to skin care in that the materials have been found to form films on the skin which possess a very low water vapor permeability enabling the materials to form a barrier on the skin which will reduce moisture loss from the stratum corneum.

The following examples illustrate the method of making cyclic alkylmethylsiloxanes.

EXAMPLE I

A suspension of 1.2 grams of 0.5% Pt/C in 120 grams of dry hexene-1 was stirred and heated to reflux. To this suspension was slowly added 80 grams of $(MeHSiO)_4$. After complete addition, the mixture was heated at 100° C. for 1 hour, then cooled and filtered to remove the Pt/C catalyst. The mixture was then heated and evacuated, removing 10 grams of excess hexene-1. The remaining material was distilled to produce 185 grams (95%) of $(C_6H_{13}MeSiO)_4$, having a boiling point of 350° C., a refractive index of 1.4374, a density of 0.90 g/ml, and a viscosity of 14 cs.

EXAMPLE II

A suspension of 1.2 grams of 0.5% Pt/C in 80 grams of dry hexene-1 was stirred and heated to reflux. To this suspension was slowly added 120 grams of a mixture of cyclic $(HMeSiO)_x(Me_2SiO)_y$ having a boiling point of 145°–165° C., wherein $x=1:y=3$, $x=2:y=2$, and $x=3:y=1$. After complete addition, the mixture was heated to 100° C. for 1 hour, then cooled and filtered to remove the Pt/C catalyst. The mixture was heated and evacuated, removing 6 grams of excess hexene-1. The remaining 190 grams of material was a liquid mixture of cyclic $(C_6H_{13}MeSiO)_x$ $(Me_2SiO)_y$, wherein $x=1:y=3$, $x=2:y=2$ and $x=3:y=1$ having a refractive index of 1.4170, a density of 0.93 g/ml, and a viscosity of 6 cs.

The following examples are set forth for the purpose of further illustrating the inventive concepts of the present invention.

EXAMPLE III

A blend was prepared by combining 13.5 grams of a high molecular weight silicone gum which was a silanol end-blocked polydimethylsiloxane gum having the formula $HO(CH_3)_2SiO[(CH_3)_2SiO]_nSi(CH_3)_2OH$, in which n had a value of about ten thousand; 1.5 grams of a cyclopolysiloxane which was a mixture of octamethylcyclotetrasiloxane $[(Me_2)SiO]_4$, and decamethylcyclopentasiloxane $[(Me_2)SiO]_5$; and eighty-five grams of an alkylmethylsiloxane having Formula I shown previously in which the value of z was five. These ingredients were mixed together at one hundred degrees Centigrade with high shear. The resulting composition was a clear blend "A" having a viscosity of two thousand centistokes measured at twenty-five degrees Centigrade.

EXAMPLE IV

For purposes of comparison, Example III was repeated and a blend "B" was prepared containing 13.5 grams of the silicone gum and 86.5 grams of the cyclopolysiloxane. Blend "B" did not contain the alkylmethylsiloxane. The viscosity of blend "B" was six thousand centistokes measured at twenty-five degrees Centigrade.

EXAMPLE V

A standard sensory test was conducted with blend "A" which is representative of the invention, and with the comparison blend "B". Five volunteers were selected to conduct the test. The test consisted of rubbing one drop of a blend onto the inside of the forearm in a circular motion for up to 120 revolutions, at a rate of one revolution per second in response to a metronome, while measuring the spreadability and stickiness of the blend. The number of rubs required to reach resistance was recorded. Following rub in, comparisons were recorded for slipperiness, residue, gloss, and smoothness, of each skin treatment. The results of these observations indicated that (i) blend "B" was more sticky than blend "A" during rub in; (ii) blend "B" required twenty more revolutions to rub in than blend "A"; and (iii) blend "A" was smoother after rub in than blend "B".

It is surprising and unexpected that the alkylmethylsiloxanes of the present invention would solvate and dissolve the high molecular weight silicone gums, and produce a lower viscosity mixture. Thus, as noted above, blend "A" included the alkylmethylsiloxane and had a viscosity of two thousand centistokes, while blend "B" which contained only the silicone gum and the cyclopolysiloxane, had a viscosity of six thousand centistokes. It would be expected that a cyclopolysiloxane such as $[(CH_3)_2SiO]_x$ would solvate and dissolve a silicone gum containing the units $—[(CH_3)_2SiO]_x—$ since these two silicone materials are elementally similar. However, an alkylmethylsiloxane is a silicone-hydrocarbon hybrid rather than a dimethylsiloxane. The presence in the alkylmethylsiloxane of a hydrocarbon constituent such as the hexyl group $C_6H_{13}$ renders these alkylmethylsiloxanes elementally different from silicone gums. Thus, the solvating capability of the alkylmethylsiloxanes in the compositions of the present invention is an added and unexpected advantage and benefit, in that compositions containing these silicone-hydrocarbon hybrids possess a lower viscosity which makes them easier to apply to the skin.

Other variations may be made in the compounds, compositions, and methods, set forth hereinabove without departing from the essential features and concepts of the present invention. It should be understood that the forms of the invention described herein are exemplary only, and are not intended to be limitations on the scope of the present invention which is defined in the appended claims.

That which is claimed is:

1. A composition comprising (i) from 30.0 to 97.8 percent by weight of an alkylmethylsiloxane having the formula

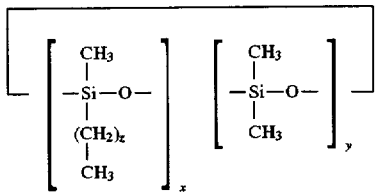

in which the sum of the integers x and y is four, five, or six, with the proviso that x and y cannot be zero; and z is an integer having a value of one to twelve; (ii) from 0.2 to fifty percent by weight of a cyclopolysiloxane having the formula $[(CH_3)_2SiO]_a$ in which a is an integer having a value of three to ten; and (iii) two to twenty percent by weight of a silicone gum selected from the group consisting of silanol end-blocked polydimethylsiloxane gums having the formula $HO(CH_3)_2SiO[(CH_3)_2SiO]_nSi(CH_3)_2OH$, and polydimethylsiloxane gums having the formula $(CH_3)_3SiO[(CH_3)_2SiO]_nSi(CH_3)_3$, in which n is an integer having a value of from five thousand to fifty thousand.

2. The composition of claim 1 in which z is 5–7.

3. The composition of claim 1 in which x is one; y is three, four, or five; and z is 5–7.

4. The composition of claim 1 in which x is two; y is two, three, or four; and z is 5–7.

5. The composition of claim 1 in which x is three; y is one, two, or three; and z is 5–7.

6. The composition of claim 1 in which x is four; y is one, or two; and z is 5–7.

7. The composition of claim 1 in which x is five; y is one; and z is 5–7.

8. The composition of claim 1 including from 83.5 to 94.5 percent by weight of the alkylmethylsiloxane, from 0.5 to 1.5 percent by weight of the cyclopolysiloxane, and from five to fifteen percent by weight of the silicone gum.

9. The composition of claim 8 in which n has a value of ten thousand to fifty thousand.

10. The composition of claim 1 in which the cyclopolysiloxane is a mixture of octamethylcyclotetrasiloxane $[(Me_2)SiO]_4$ and decamethylcyclopentasiloxane $[(Me_2)SiO]_5$.

11. A method of conditioning human skin comprising applying an effective amount of the composition of claim 1 to the skin as a coating, and rubbing the composition into the skin.

12. A method according to claim 11 in which the coating is applied in the form of a lotion, and the lotion includes from one to ten percent by weight of the composition of claim 1.

13. A composition comprising (i) from 30.0 to 97.8 percent by weight of an alkylmethylsiloxane having the formula

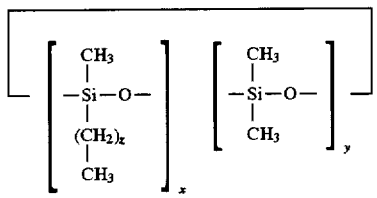

in which the sum of the integers x and y is four, five, or six, with the proviso that x and y cannot be zero; and z is an integer having a value of 5–7; (ii) from 0.2 to fifty percent by weight of a cyclopolysiloxane having the formula $[(CH_3)_2 SiO]_a$ in which a is an integer having a value of three to ten; and (iii) two to twenty percent by weight of a silicone gum selected from the group consisting of silanol endblocked polydimethylsiloxane gums having the formula $HO(CH_3)_2 SiO[(CH_3)_2SiO]_nSi(CH_3)_2OH$, and polydimethylsiloxane gums having the formula $(CH_3)_3SiO[(CH_3)_2SiO]_n Si(CH_3)_3$, in which n is an integer having a value of from five thousand to fifty thousand.

14. The composition of claim 13 in which x is one and y is three, four, or five.

15. The composition of claim 13 in which x is two and y is two, three, or four.

16. The composition of claim 13 in which x is three and y is one, two, or three.

17. The composition of claim 13 in which x is four and y is one or two.

18. The composition of claim 13 in which x is five and y is one.

19. A method of conditioning human skin comprising applying an effective amount of the composition of claim 13 to the skin as a coating, and rubbing the composition into the skin.

20. A method according to claim 19 in which the coating is applied in the form of a lotion, and the lotion includes from one to ten percent by weight of the composition of claim 13.

* * * * *